US006274778B1

(12) United States Patent
Moraly et al.

(10) Patent No.: US 6,274,778 B1
(45) Date of Patent: Aug. 14, 2001

(54) PULVERULENT SORBITOL AND ITS PROCESS OF PREPARATION

(75) Inventors: Franck Moraly, Lestrem; Erik Labergerie, Armentieres; José Lis, La Gorgue; Philippe Lefevre, Merville; Frédéric Bouvier, Lille, all of (FR)

(73) Assignee: Roquette Freres, Lestrem (FR)

( * ) Notice: Subject to any disclaimer, the term of this patent is extended or adjusted under 35 U.S.C. 154(b) by 0 days.

(21) Appl. No.: 09/457,536

(22) Filed: Dec. 9, 1999

(30) Foreign Application Priority Data

Dec. 11, 1998 (FR) .................................................. 98 15681

(51) Int. Cl.⁷ .................................................. C07C 31/18
(52) U.S. Cl. .......................... 568/852; 568/853; 424/440; 426/660
(58) Field of Search ..................... 568/851, 852, 568/853; 426/660; 424/400, 440, 489

(56) References Cited

U.S. PATENT DOCUMENTS

| 3,308,171 | * | 3/1967 | Oikawa . | |
|---|---|---|---|---|
| 3,384,546 | | 5/1968 | Palermo et al. . | |
| 4,252,794 | * | 2/1981 | DuRoss | 424/176 |
| 4,507,511 | * | 3/1985 | Reiff et al. | 568/852 |
| 4,605,794 | * | 8/1986 | Reiff et al. | 568/582 |
| 4,831,129 | | 5/1989 | Serpelloni . | |
| 5,573,777 | * | 11/1996 | Serpelloni et al. | 424/440 |
| 5,939,091 | * | 8/1999 | Eoga et al. | 424/464 |

FOREIGN PATENT DOCUMENTS 0 032 288   7/1981   (EP) .
2 046 743  11/1980   (GB) .

OTHER PUBLICATIONS

CA:66:12103 abs of DD49322, Aug. 1966.*
Abstract in English of patent FR 2 622 190 Apr. 1989.
Brunauer S., Journal of the American Chemical Society, 1938, 60, pp 309–319.

* cited by examiner

Primary Examiner—Jean F. Vollano
(74) Attorney, Agent, or Firm—Henderson & Sturm LLP

(57) ABSTRACT

The invention relates to a pulverulent sorbitol, characterized in that it exhibits a hygroscopicity value, determined according to a test A, of less than 2%, preferably of less than 1.7%, and a specific surface, determined according to the BET method, at least equal to 2 m²/g, preferably at least equal to 2.2 m²/g, and also relates to its process of preparation. The invention also relates to compositions intended in particular for the food and pharmaceutical fields and to the use of the said pulverulent sorbitol in the preparation of tablets exhibiting a <<smooth in the mouth>> texture.

12 Claims, No Drawings

PULVERULENT SORBITOL AND ITS PROCESS OF PREPARATION

CROSS-REFERENCE TO RELATED APPLICATIONS

Not Applicable.

STATEMENT REGARDING FEDERALLY SPONSORED RESEARCH OR DEVELOPMENT

Not Applicable.

BACKGROUND OF THE INVENTION

1. Field of the Invention

A subject-matter of the present invention is a pulverulent sorbitol of low hygroscopicity and of high specific surface which furthermore exhibits a low relative density, a specific particle size and an excellent ability to flow.

The invention also relates to a pulverulent sorbitol, the technical properties of which for use in direct compression are improved, and to a process for its preparation.

2. Description of the Prior Art

Sorbitol is a hexitol mainly used in the fields of food and pharmaceutical applications as a sweetening agent but also for its reduced calorific value and its acariogenicity.

Pulverulent sorbitol, just like other pulverulent polyols, such as xylitol or mannitol, is, for its part, commonly used as a pharmaceutical excipient, as a sweetener and texturizing agent in the food industry, and as an additive vehicle in industries of all types. However, it is a better excipient than xylitol and mannitol, in particular in compression, because of its specific ability to crystallize in the form of needle-shaped crystals which are directly compressible.

Generally, in order to have available a crystalline sorbitol of high compressive strength, every effort is made to manufacture a sorbitol of $\gamma$ crystalline form (the $\alpha$ and $\beta$ forms are particulary unstable) by processing a supersaturated solution of sorbitol, the $\gamma$ form of which represents at least 90%. However, even when it is crystallized in this, most stable, $\gamma$ form, the pulverulent sorbitol obtained conventionally exhibits a number of disadvantages, including that of being very hygroscopic.

This high hygroscopicity has the effect of rendering the flow of pulverulent sorbitol difficult, indeed even impossible, as soon as water uptake has occurred. Its use in direct compression is then found to be limited by this, requiring, for example, serious difficulties to be overcome in filling presses in the manufacture of lozenges or tablets.

In order to avoid this flow problem of pulverulent sorbitol, the preparation has been recommended of a sorbitol of low relative density and of coarser particle size, as disclosed in Patent FR 1,506,334.

However, it is established that the lower the bulk density of a pulverulent sorbitol, the greater the friability of the latter, that is to say the greater its sensitivity to a detrimental change in its particle size by mechanical action. In addition, the dissolution times of this pulverulent product of coarse particle size are generally too long and therefore unsuitable.

Finally, while the ability to flow is partially improved by the use of particles of such a particle size, the residual hygroscopic nature, which is still too high, in all cases renders the use of this pulverulent sorbitol out of the question when it is used in combination with ingredients or additives which are very sensitive to water.

It is also established that the ability to fix significant amounts of additive is a direct function of the specific surface of the said particles. The absorption capabilities of pulverulent sorbitol thus increase in proportion as its specific surface increases. However, it is known that the specific surface of the dense crystals of commercial $\gamma$ sorbitol is very low. Thus, for a particle size of between 500 and 1000 $\mu$m, it is very low, i.e. at most equal to 0.7 $m^2/g$.

With the aim of preparing a pulverulent sorbitol exhibiting an improved particle size and a good ability to flow and satisfying the desired conditions of compressibility and friability, Patent Application FR 2,622,190 discloses a sorbitol powder comprising particles with a mean diameter of between 300 and 500 $\mu$m. However, the high bulk density and the relatively low specific surface of the said particles, of the order of 0.9 to 1.2 $m^2/g$, are not in fact significantly modified by the manufacturing process employed, so that the pulverulent sorbitol thus obtained retains the same moisture absorption factor and the same solubility in water as the starting sorbitol powder.

Patent EP 32,288 discloses a $\gamma$ sorbitol polymorph, with a disintegrated and loose crystalline structure, which exhibits an improved hygroscopicity and satisfactory compressive properties. However, these specific properties only relate to a particle size fraction of between 250 and 841 $\mu$m (i.e. 20/60 mesh), the specific surface of which is, in any case, less than 2 $m^2/g$.

It emerges, from everything which precedes, that there exists an unsatisfied need to have available a pulverulent sorbitol which simultaneously exhibits the advantages, generally incompatible, of low hygroscopicity, on the one hand, and of high specific surface, on the other hand, or of low bulk density, on the one hand, and of low friability, on the other hand, for a relatively low particle size.

There is therefore a need for a novel pulverulent sorbitol capable of reconciling all of the aforementioned objectives.

DETAILED DESCRIPTION OF THE INVENTION

The pulverulent sorbitol in accordance with the invention is thus first of all characterized in that it exhibits:

a hygroscopicity value, determined according to a test A, of less than 2%, preferably of less than 1.7%, a specific surface, determined according to the BET method, at least equal to 2 $m^2/g$, preferably at least equal to 2.2 $m^2/g$.

Its hygroscopicity, determined according to the test A, is preferably between 0.5 and 1.6%, preferably between 0.9 and 1.4%.

The test A consists in drawing up the isothermal curve for water sorption at 20° C. which expresses the percentage of water uptake of a pulverulent product, dehydrated beforehand, which is placed in an atmosphere of variable relative humidity and at a temperature of 20° C. The determination of the hygroscopicity of the pulverulent product will then be the percentage of water uptake at 60% equilibrium relative humidity (or 60% E.R.H.).

The specific surface is determined over the entire particle size distribution of the pulverulent sorbitol by virtue of a Quantachrome specific surface analyser based on a test of absorption of nitrogen on the surface of the product subjected to analysis, the technique described in the BET article, Surface Area by Nitrogen Absorption, by S. Brunauer et al. (Journal of the American Chemical Society, 60, 309, 1938), being followed.

It is particularly surprising that a pulverulent sorbitol can jointly exhibit a specific surface at least equal to 2 $m^2/g$, preferably at least equal to 2.2 $m^2/g$, and a hygroscopicity of less than 2%, preferably of less than 1.7%. This is because it is very conventionally accepted that the hygroscopicity of a pulverulent product increases with its specific surface, i.e. its surface exposed to the environment comprising water vapour.

In point of fact, the pulverulent sorbitol in accordance with the invention exhibits a high specific surface characteristic of a granulated product with, nevertheless, a low hygroscopicity characteristic of a product crystallized in a stable crystalline form.

By way of examples, the sorbitol sold by the company Merck under the name Sorbitol grade L exhibits a hygroscopicity of 2.4% at 60% ERH according to the test A, for a specific surface according to the BET method of 1.55 $m^2/g$, and the sorbitol sold by the Applicant Company under the trade name Neosorb® P 60 W exhibits a hygroscopicity, under the same measuring conditions, with a value of 1.53% for a specific surface of less than 1 $m^2/g$.

Surprisingly and unexpectedly, and in contrast to what was expected, the pulverulent sorbitol in accordance with the invention exhibits a strikingly lower hygroscopicity than that which is conventionally described for commercial pulverulent sorbitols exhibiting the highest specific surfaces. The result of this is that the pulverulent sorbitol in accordance with the invention has much better properties, in particular as additive vehicle, than a standard pulverulent sorbitol. These properties are due, at least in part, to the particularly high specific surface of this product.

The Applicant Company therefore regards as novel a pulverulent sorbitol, characterized in that it exhibits a specific surface, according to the BET method, of greater than 2.5 $m^2/g$, preferably of between 2.6 and 4 $m^2/g$, and more preferably still of between 2.6 and 3.5 $m^2/g$.

The pulverulent sorbitol in accordance with the invention can also be characterized by its bulk density, its direct compression properties and its friability.

The bulk density is determined by the use of a device sold by the company Hosokawa under the trade name Powder Tester, the recommended method for measuring a bulk density being applied.

Under these conditions, the pulverulent sorbitol in accordance with the invention exhibits a low bulk density, that is to say of between 0.35 and 0.65 g/ml, preferably of between 0.4 and 0.6 g/ml.

The compressibility of the pulverulent sorbitol is determined according to the following test B described in Patent EP 220,103, of which the Applicant Company is the proprietor. This test B consists in measuring the force, expressed in newtons, which is representative of the compressibility of the pulverulent sorbitol studied. This force therefore expresses, in this instance, the resistance to crushing of a tablet which is cylindrical with convex faces (radius of curvature of 14 mm), with a diameter of 13 mm, with a thickness of 6 mm and with a weight of 0.647 g, i.e. with a bulk density of 1.1 g/ml.

The compressibility of the pulverulent sorbitol in accordance with the invention is determined at a value generally of between 100 and 150 N, more particularly at a value of between 120 and 140 N.

The friability of the pulverulent sorbitol in accordance with the invention is, for its part, determined according to a test C described in Patent EP 645,096, of which the Applicant Company is the proprietor. The U.S. counterpart of EP 645,096 : U.S. Pat. No. 5,573,777 is incorporated herein by reference, and describes the friability test (test C) at column 5 lines 22–43. It exhibits a value generally of between 10 and 50%, preferably of between 20 and 40%.

This friability value is all the more remarkable since the pulverulent sorbitol in accordance with the invention exhibits a low relative density. This is because it is conventionally accepted that a pulverulent sorbitol will decrease in friability in proportion as its relative density and its compressibility increase.

Because of this high compressibility, the mechanical strength of the tablets obtained with the said pulverulent sorbitol is indeed particularly high, in comparison with that of the tablets obtained with the commercial products. By way of example, the sorbitol powder grades sold by the company DHW Rodleben, with a relative density equal to 0.6 g/ml, exhibit a compressibility, determined according to the test B, in the region of 100 N.

The low relative density of the pulverulent sorbitol in accordance with the invention and its feature of high mechanical strength make it possible to advantageously reduce the material employed in the manufacture of the tablets or lozenges, thereby significantly decreasing the production costs.

As regards the friability, surprisingly and unexpectedly, and in contrast to what is commonly accepted, the pulverulent sorbitol in accordance with the invention does not conform to the rule according to which, the lower the bulk density of a pulverulent sorbitol, the higher its friability.

These improved properties of compressibility and of friability, combined with the features of low hygroscopicity and of high specific surface, have in particular the consequence of rendering the pulverulent sorbitol in accordance with the invention particularly well suited to food, pharmaceutical or other applications requiring the fixing of significant amounts of additives. Its adsorption capabilities, which are markedly greater than those of the conventionally known compressible sorbitols, therefore allow it, furthermore, to act as a vehicle for additives which are particularly soluble in water, such as vitamins, colorants or powerful sweeteners.

Furthermore, the pulverulent sorbitol in accordance with the invention can also be characterized by its mean diameter, its uniformity of particle size distribution and its ability to flow, these properties being particularly suitable for the said compressive applications. Thus, the pulverulent sorbitol according to the invention generally exhibits a mean diameter of between 150 and 250 μm and a particle size distribution of between 60 and 500 μm. These values are determined on a Coulter® Laser LS particle sizer.

Furthermore, it should be emphasized that the not insignificant advantages of the use of the pulverulent sorbitol in accordance with the invention which are cited above constitute a combination of properties which the products of the prior art never simultaneously possess. Mention may be made, among these advantages, of its ability to flow.

This ability to flow is evaluated by using the Powder Tester device sold by the company Hosokawa. This device makes it possible to measure, under standardized and reproducible conditions, the ability to flow of a powder and to calculate a flow grade, also known as the Carr index.

The pulverulent sorbitol in accordance with the invention exhibits an excellent flow grade generally of at least 70, preferably of between 70 and 90, and more preferably of between 70 and 80. This value is slightly greater than those of the sorbitol powders of the prior art obtained by granulation. This is all the more remarkable since, with respect to these prior products, the pulverulent sorbitol in accordance with the invention exhibits a finer particle size.

From the view point of its chemical composition, the pulverulent sorbitol in accordance with the invention is relatively pure, that is to say that it exhibits a high sorbitol content generally of greater than 95% and more particularly of greater than 98% by weight.

This high content is also expressed by a high melting point, determined by microcalorimetric analysis (DSC), of between 98 and 99.5° C., more particularly of between 98.9 and 99.2° C., which is among the highest values ever measured for sorbitol powders used in direct compression.

Without wishing to be bound by any one theory, it may be thought that the physicochemical characteristics cited above for the pulverulent sorbitol in accordance with the invention explain its excellent ability to flow. These characteristics relate in particular to its sorbitol content, its centred particle size and its low hygroscopicity but also to the characteristic shape of its particles. As regards the latter point, observation under a scanning electron microscope at low magnification (magnitude 50) reveals that the pulverulent sorbitol in accordance with the invention is generally composed of particles with variable shapes exhibiting few sharp edges which are predominantly composed of microparticles agglomerated to one another. At higher magnification (magnitude 1500), the said particles exhibit, at their surface, numerous fine needles of γ sorbitol without specific orientation, which is characteristic of copious surface recrystallization, and wide regions with a more molten appearance, the relative size of which can be attributed to the alternative forms of the processes employed in their manufacture.

The latter characteristics can contribute to explaining the excellent ability to flow of the pulverulent sorbitol in accordance with the invention and make it possible, in all cases, to also distinguish it from the commercial pulverulent sorbitols.

To the knowledge of the Applicant Company, these specific shapes have never been described for a pulverulent sorbitol. The pulverulent sorbitol in accordance with the invention is therefore easily distinguished from a pulverulent sorbitol obtained by simple atomization, which is composed of essentially spherical particles, or from a sorbitol obtained by extrusion, which comprises angular particles in the form of clusters of fine needles oriented in the same direction.

The pulverulent sorbitol in accordance with the invention is capable of being obtained by carrying out a stage of granulation of a sorbitol powder by the wet route using a binder and then a stage of maturing by drying the granulated sorbitol thus obtained. In order to obtain a pulverulent sorbitol in accordance with the invention having the stated functional characteristics, the Applicant Company has found that it is advisable to choose, as starting sorbitol, a sorbitol powder which can be obtained by granulation, by atomization, by extrusion or by crystallization from water or from another solvent, such as alcohol. The particle size of the said starting sorbitol powder does not constitute per se a limiting factor in producing a pulverulent sorbitol in accordance with the invention.

The binder, for its part, is composed of water or of a sorbitol syrup with a solids content at most equal to 100%, preferably of between 10 and 80%.

Surprisingly and unexpectedly, the Applicant Company has found that the granulation of a sorbitol powder by the wet route using a binder makes it possible to prepare, with a high yield, a product in accordance with the invention with regard to its hygroscopicity, its specific surface, its relative density, its particle size and its ability to flow. This is because the processes described previously do not make it possible to obtain all the desired characteristics.

In order to carry out the granulation, use may be made, for example, of a continuous mixer-granulator of vertical Flexomix type sold by the company Hosokawa Schugi or of horizontal CB type sold by the company Lödige, into which mixer-granulator is continuously introduced, via a weight metering device, the starting sorbitol powder to be granulated and into which mixer-granulator is continuously introduced, via a volumetric metering device, the binder (water or the sorbitol solution). The granulation can also be carried out in an atomization tower or in a fluidized bed granulator.

According to a first preferred embodiment of the process for the preparation of a pulverulent sorbitol in accordance with the invention, the choice is made of the use of a Hosokawa Schugi continuous mixer-granulator of vertical Flexomix type. The starting sorbitol powder and the binder are very intimately mixed in the mixer-granulator, which is equipped with a shaft with knives arranged as blades and with a system for spraying liquids via injection nozzles.

In a preferred form of the process, the satisfactory dispersion of the constituents and the agglomeration of the particles of the starting sorbitol powder are achieved by high speed stirring, i.e. stirring with a value at least equal to 1500 rpm, preferably at least equal to 3000 rpm. At the outlet of the mixer-granulator, the granules formed are discharged continuously onto a dryer. Discharging is preferably carried out by gravity in the case of the said vertical granulator and by thrusting, via the axis of the rotary knives, if the horizontal granulator is used.

This second stage of drying at the outlet of the mixer-granulator makes it possible to remove the water originating from the binder and to crystallize the dry matter originating from the binder, in the case where a sorbitol solution has been employed, so that crystallization takes place after the prior stage of granulation. The dryer can be, for example, a fluidized bed dryer or a maturing rotary drum. The pulverulent sorbitol in accordance with the invention is obtained after cooling and optionally sieving. In this case, the fine particles can be directly recycled at the start of granulation and the coarse particles can be milled and recycled at the start of sieving or at the start of granulation.

In a second preferred embodiment of the process for the preparation of a pulverulent sorbitol in accordance with the invention, the choice is made to carry out the granulation of the sorbitol powder by the wet route in an atomization tower. Crystalline sorbitol is then introduced into the said atomization tower and water or a sorbitol syrup with a solids content at most equal to 100%, preferably of between 10 and 80% by weight, is added as binder.

The choice is made to feed an MSD (Multi-Stage Dryer) atomization tower, with a water evaporation capacity of the order of 350 kg/h, with sorbitol powder at a throughput of between 400 and 600 kg/h, the granulation taking place with water as binder, as will be exemplified below.

In the light of the melting points of the various crystalline forms of sorbitol, the Applicant Company has found that it is necessary to carefully monitor the operating temperatures of the atomization tower.

The choice is therefore advantageously made to adjust the temperature of the feed air to a value of between 140 and 145° C., the temperature of the mists to a value of between 70 and 75° C. and the temperature of the static bed to a value of between 70 and 80° C.

The pulverulent sorbitol in accordance with the invention can advantageously be employed, because of the quality of its functional properties mentioned above, in the <<tablets to be sucked>> application.

This is because the tablets prepared from the said sorbitol exhibit, in addition to a high compressibility which is reflected by high hardness for a low relative density, a <<smooth in the mouth>> texture. The latter organoleptic property is particularly appreciated in the manufacture of lozenges or tablets, as a <<rough>> characteristic for tablets is regarded as a non-pleasurable feature by experts in this field.

Other characteristics and advantages of the invention will become apparent on reading the examples which follow. However, they are given here only by way of illustration and without implied limitation.

EXAMPLE 1

A Schugi vertical Flexomix mixer-granulator is fed continuously via a powder metering device, at a throughput of 500 kg/h, with a sorbitol powder manufactured by granulation.

Furthermore, the mixer-granulator is fed continuously with water at 60° C. and at a throughput of 40 l/h via a spray nozzle. The rotating shaft with knives is adjusted beforehand to a speed of 3000 rpm. The wet granulated powder at the outlet of the mixer-granulator falls continuously, by gravity, into a Schugi fluidized bed dryer with two compartments.

In the first compartment, the granulated product is dried by air at 120° C. and then it is cooled by air at 20° C. in the second compartment. The dried and cooled granulated product is subsequently sieved continuously on a rotary screen equipped with two metal cloths of 120 and 600 µm. The starting sorbitol powder A and the pulverulent sorbitol B thus obtained in accordance with the invention exhibit the characteristics combined in the following Table I.

TABLE I

| Parameters | A | B |
| --- | --- | --- |
| Sorbitol content (% by weight) | 98.5 | 98.5 |
| Water content (%) | 0.5 | 0.4 |
| Melting temperature (according to DSC; ° C.) | 98.5 | 99.2 |
| Heat of fusion (according to DSC; J/g) | 168 | 171 |
| Hygroscopicity (% at 60% ERH) | 1.7 | 1.3 |
| Specific surface (m$^2$/g) | 0.8 | 2.4 |
| Bulk density (g/ml) | 0.61 | 0.5 |
| Mean diameter (µm) | 100 | 155 |
| Flow grade (value/100) | 65 | 75 |
| Compressibility (N) | 60 | 120 |
| Friability (%) | 18 | 26 |

EXAMPLE 2

A Schugi vertical Flexomix mixer-granulator is fed continuously via a powder metering device with the starting sorbitol powder A under the same conditions as in Example 1 but the said mixer-granulator is fed, at a throughput of 40 /h and a temperature of 60° C., via a spray nozzle, with a sorbitol solution with a solids content of 70% as binder.

The pulverulent sorbitols C and D in accordance with the invention, obtained respectively with a temperature of the heating air of 120° C. and 75° C., exhibit the characteristics combined in the following Table II.

TABLE II

| Parameters | C | D |
| --- | --- | --- |
| Sorbitol content (% by weight) | 98.5 | 98.5 |
| Water content (%) | 0.45 | 0.55 |
| Melting temperature (according to DSC; ° C.) | 98.9 | 99.2 |
| Heat of fusion (according to DSC; J/g) | 172 | 175 |

TABLE II-continued

| Parameters | C | D |
| --- | --- | --- |
| Hygroscopicity (% at 60% ERH) | 1.2 | 1.4 |
| Specific surface (m$^2$/g) | 2.75 | 2.2 |
| Bulk density (g/ml) | 0.47 | 0.42 |
| Mean diameter (µm) | 192 | 193 |
| Flow grade (value/100) | 75 | 74 |
| Compressibility (N) | 120 | 130 |
| Friability (%) | 25 | 22 |

EXAMPLE 3

The process is carried out in the same way as in Example 1 but with a starting sorbitol powder with a finer particle size. The starting sorbitol powder E and the pulverulent sorbitol F in accordance with the invention exhibit the characteristics combined in the following Table III.

TABLE III

| Parameters | E | F |
| --- | --- | --- |
| Sorbitol content (% by weight) | 98 | 98 |
| Water content (%) | 0.5 | 0.3 |
| Melting temperature (according to DSC; ° C.) | 97.5 | 99.2 |
| Heat of fusion (according to DSC; J/g) | 168 | 169 |
| Hygroscopicity (% at 60% ERH) | 1.9 | 1.1 |
| Specific surface (m$^2$/g) | 0.9 | 3.25 |
| Bulk density (g/ml) | 0.5 | 0.48 |
| Mean diameter (µm) | 60 | 199 |
| Flow grade (value/100) | 60 | 78.5 |
| Compressibility (N) | 65 | 122 |
| Friability (%) | nd | 32 |

EXAMPLE 4

The process is carried out with the same starting sorbitol powder E as was employed in Example 3. An MSD atomization tower with an evaporation capacity of 350 kg/h is fed with the sorbitol powder E at the rate of 410 kg/h.

The granulation with water is carried out by spraying water at the rate of 80 l/h via a nozzle at a pressure of 45 bar.

The drying air enters at 136° C. and leaves at 78° C. and the temperature of the mists is determined at 142° C., the static bed at the bottom of the tower being cooled by air at 70° C.

At the outlet of the atomization tower, the product passes onto a vibrated fluid bed where it is cooled by air in 3 temperature regions fixed respectively at 35° C., 20° C. and 20° C.

The product G exhibits the characteristics combined in the following Table IV:

TABLE IV

| Parameters | E | G |
| --- | --- | --- |
| Sorbitol content (% by weight) | 98 | 98 |
| Water content (%) | 0.5 | 0.25 |
| Melting temperature (according to DSC; ° C.) | 97.5 | 99 |
| Heat of fusion (according to DSC; J/g) | 168 | 169 |
| Hygroscopicity (% at 60% ERH) | 1.9 | 1 |
| Specific surface (m$^2$/g) | 0.9 | 3.25 |
| Bulk density (g/ml) | 0.5 | 0.47 |
| Mean diameter (µm) | 60 | 200 |
| Flow grade (value/100) | 60 | 80 |
| Compressibility (N) | 65 | 125 |
| Friability (%) | nd | 30 |

EXAMPLE 5

Products in accordance with the invention, prepared by applying the processes described in Examples 1 to 4, are compared, in the following Table V, with pulverulent sorbitols already known.

TABLE V

|  | Products in accordance with the invention | Comparative products | | |
| --- | --- | --- | --- | --- |
|  |  | Neosorb P60W Roquette | Sorbitol-L Merck | Sorbitol disclosed in FR 2,622,190 |
| Sorbitol content (% by weight) | 98–100 | 94.5–97.8 | 97.7–98 | 97.2–98.2 |
| Water content (%) | 0.35–0.45 | 0.5 | 0.6–0.8 | <1 |
| Melting temperature (DSC; ° C.) | 98.9–99.2 | 94.5–98 | 94.8–95 | 94.5–96 |
| Heat of fusion (DSC; J/g) | 165–175 | 165 | 155–165 | — |
| Hygroscopicity (% at 60% ERH) | 1.1 to 1.4 | 1.53 | 2.40 | — |
| Specific surface ($m^2/g$) | 2.2–3.25 | <1 | 1.55 | 2–1.2 |
| Mean diameter ($\mu m$) | 150–250 | 240–340 | 270–300 | 280–520 |
| Bulk density (g/ml) | 0.4–0.6 | 0.4–0.65 | 0.45 | 0.54–0.6 |
| Flow grade (value/100) | 70–80 | 75 | 78 | — |
| Compressibility (N) | 120–130 | 40 | 150 | 100 |
| Friability (%) | 20–35 | 20 | 50 | 45 |

The pulverulent sorbitols in accordance with the invention all possess, in contrast to the products of the prior art, excellent functional properties which make them suitable for use without disadvantage as nonhygroscopic excipients and vehicles for additives, in particular in the food and pharmaceutical industries.

EXAMPLE 6

The effect of the pulverulent sorbitol in accordance with the invention, relative to the sorbitol of the prior art, on the texture in the mouth of tablets prepared from the said sorbitols is evaluated by sensory analysis. This organoleptic test D is carried out in the following way.

For each pulverulent sorbitol, in this case a sorbitol sold by the company Merck under the name Sorbitol grade L and a sorbitol in accordance with the invention prepared according to Example 1, a series of convex tablets with a diameter of 13 mm is prepared, which tablets are obtained on a Frogerais AM reciprocating press, after mixing at the time of tableting with 0.7% of magnesium stearate.

Each series is then evaluated <<blind>> by an expert jury of 10 people. The latter are then to pronounce on the <<smooth in the mouth>> character of the said sucked tablets. By bringing together the evaluations obtained for each type of tablet manufactured from the sorbitol in accordance with the invention, it is possible to compare them with those prepared with the sorbitol of the prior art, according to the following grading:

grading <<--->>: <<smooth in the mouth>> texture not perceptible; on the contrary, pronounced rough character, grading <<++>>: markedly perceptible <<smooth in the mouth>> texture but with a slight rough character feeling, grading <<+++>>: perceptible <<smooth in the mouth>> texture, without any rough character feeling.

The results of these tests relating to the pleasurable character of the tablets prepared from the pulverulent sorbitols are collated in Table VI below as a function of the parameters of weight, of relative density and of hardness of the tablets used.

TABLE VI

| Type of sorbitol used | Weight (mg) of the tablets | Relative density (mg/ml) of the tablets | Hardness (N) of the tablets | Surface which is smooth in the mouth |
| --- | --- | --- | --- | --- |
| Sorbitol L Merck | 652 | 1.154 | >196 | --- |
| Pulverulent sorbitol in accordance with the invention | 651 | 1.152 | 161 | ++ |
|  | 686 | 1.214 | >196 | +++ |

It is found that the tablets manufactured with the pulverulent sorbitol in accordance with the invention differ from the tablets manufactured with the other sorbitol in that they simultaneously exhibit a high compressibility (high hardness for a low relative density) and a <<smooth in the mouth>> texture.

What is claimed is:

1. Pulverulent sorbitol, the crystalline form of which is the γ form, having a sorbitol content higher than 95%, which exhibits:

a hygroscopicity value, determined according to a test A, of less than 2%, said test A consisting in drawing the isothermal curve for water sorption at 20° C. which expresses the percentage of water uptake of a pulverulent product, dehydrated beforehand, which is placed in an atmosphere of variable relative humidity and at a temperature of 20° C., the hygroscopicity value being the percentage of water uptake at 60% equilibrium relative humidity, a specific surface, determined according to the BET method, at least equal to 2 $m^2/g$.

2. Pulverulent sorbitol, the crystalline form of which is the γ form, having a sorbitol content higher than 95%, which exhibits a specific surface according to the BET method of greater than 2.5 $m^2/g$.

3. The pulverulent sorbitol according to claim 1, which exhibits a hygroscopicity value of between 0.5% and 1.6%.

4. The pulverulent sorbitol according to claim 1, which exhibits:

a bulk density, determined according to the Hosokawa method, of between 0.35 g/ml and 0.65 g/ml, a compressibility, determined according to a test B, of between 100 N and 150 N, said test B consisting in measuring the force, expressed in newtons, which expresses the resistance to crushing of a tablet which is cylindrical with convex faces, with a radius of curvature of 14 mm, a diameter of 13 mm, a thickness of 6 mm and a weight of 0.647 g, i.e. with a bulk density of 1.1 g/ml, and a friability, determined according to a test C, of between 10% and 50%, said test C comprising subjecting about 15 g of pulverulent sorbitol to be tested, having a particle size within a range of about 100 to about 200 microns, for about 15 minutes, to mechanical action in a ERWEKA TAP friabilimeter, rotating at a uniform rotational speed of 25 revolutions per minute, into which 5 substantially identical steel bells with a diameter of about 17 mm and with a weight of about 18.77 g have been introduced, the friability being a percentage of powder not retained after the test on a sieve with a mesh size of 100 microns.

5. The pulverulent sorbitol according to claim 1, which exhibits:
   a mean diameter of between 150 μm and 250 μm, and
   a flow grade of at least 70.

6. The pulverulent sorbitol according to claim which exhibits:
   a melting point of between 98° C. and 99.5° C.,
   a crystalline organization in which copious fine needles of γ sorbitol without specific orientation are found at the surface of particles of variable shapes, in combination with regions with a more molten appearance.

7. Sweetening agent, texturizing agent, or additive excipient or vehicle in compositions for the food and pharmaceutical fields, containing pulverulent sorbitol according to claim 1.

8. The pulverulent sorbitol according to claim 2, which exhibits a hygroscopicity value of between 0.5% and 1.6%.

9. The pulverulent sorbitol according to claim 2, which exhibits:
   a bulk density, determined according to the Hosokawa method, of between 0.35 g/ml and 0.65 g/ml,
   a compressibility, determined according to a test B, of between 100 N and 150 N, said test B consisting in measuring the force, expressed in newtons, which expresses the resistance to crushing of a tablet which is cylindrical with convex faces, with a radius of curvature of 14 mm, a diameter of 13 mm, a thickness of 6 mm and a weight of 0.647 g, i.e. with a bulk density of 1.1 g/ml, and
   a friability, determined according to a test C, of between 10% and 50%, said test C comprising subjecting about 15 g of pulverulent sorbitol to be tested, having a particle size within a range of about 100 to about 200 microns, for about 15 minutes, to mechanical action in a ERWEKA TAP friabilimeter, rotating at a uniform rotational speed of 25 revolutions per minute, into which 5 substantially identical steel bells with a diameter of about 17 mm and with a weight of about 18.77 g have been introduced, the friability being a percentage of powder not retained after the test on a sieve with a mesh size of 100 microns.

10. The pulverulent sorbitol according to claim 2, which exhibits:
    a mean diameter of between 150 μm and 250 μm, and
    a flow grade of at least 70.

11. The pulverulent sorbitol according to claim 2, which exhibits:
    a melting point of between 98° C. and 99.5° C.,
    a crystalline organization in which copious fine needles of γ sorbitol without specific orientation are found at the surface of particles of variable shapes, in combination with regions with a more molten appearance.

12. Sweetening agent, texturizing agent, or additive excipient or vehicle in compositions for the food and pharmaceutical fields, containing pulverulent sorbitol according to claim 2.

* * * * *